United States Patent [19]
Polvani

[11] Patent Number: 5,762,064
[45] Date of Patent: Jun. 9, 1998

[54] MEDICAL MAGNETIC POSITIONING SYSTEM AND METHOD FOR DETERMINING THE POSITION OF A MAGNETIC PROBE

[75] Inventor: Donald G. Polvani, Arnold, Md.

[73] Assignee: Northrop Grumman Corporation, Los Angeles, Calif.

[21] Appl. No.: 376,988

[22] Filed: Jan. 23, 1995

[51] Int. Cl.$^6$ ..................................................... A61B 5/05
[52] U.S. Cl. .................... 128/653.1; 324/244; 324/260; 128/899
[58] Field of Search ................... 128/653.1, 654, 128/897, 899, 903, 656–658, 737; 324/244, 246, 248, 256, 259, 260, 207.11, 207.13, 207.17

[56] References Cited

U.S. PATENT DOCUMENTS

| | | |
|---|---|---|
| 4,416,289 | 11/1983 | Bresler . |
| 4,445,501 | 5/1984 | Bresler . |
| 4,837,489 | 6/1989 | McFee ................................. 324/260 |
| 4,913,152 | 4/1990 | Ko et al. ........................... 128/653.1 |
| 5,057,095 | 10/1991 | Fabian . |
| 5,105,829 | 4/1992 | Fabian . |
| 5,318,025 | 6/1994 | Dumoulin . |
| 5,353,807 | 10/1994 | DeMarco ................................. 128/899 |
| 5,386,828 | 2/1995 | Owens et al. ...................... 128/653.1 |
| 5,442,289 | 8/1995 | Dilorio et al. ..................... 128/653.1 |
| 5,456,718 | 10/1995 | Szymaitis ............................... 128/899 |

FOREIGN PATENT DOCUMENTS

| 4215901 | 8/1993 | Germany ................................. 128/899 |
|---|---|---|
| 4023647 | 10/1994 | WIPO ................................. 128/653.1 |

OTHER PUBLICATIONS

Ahonen et al., 122–Channel SQUID Instrument for investigating the magnetic signals from the human brain, Physica Scripta, VT49A, pp. 198–205, 1993

Ribeiro et al., SQUID arrays for simulaneous magnetic measurements: Calibration and Source Localization Performance, IEEE transactions on Biomedical Engineering, v 35 n 7, pp. 551–560, Jul. 1988.

*Primary Examiner*—Brian L. Casler
*Attorney, Agent, or Firm*—Walter G. Sutcliff

[57] ABSTRACT

A medical magnetic positioning system and method for determining the position of a magnetic probe inside a body of an individual in which at least two spaced magnetometers are fastened to an area on an external portion of an individual's body proximate to the desired location of the probe inside of the body, the magnetic probe is inserted inside the body of the individual to be spaced from the at least two magnetometers, the three-dimensional magnetic field of the probe is detected at the at least two magnetometers, and the location of the probe is determined in accordance with the location of the detected three-dimensional field. Preferably the magnetometers are triaxial magnetometers adapted to be mounted on an external portion of the body proximate to the inserted location of the probe so that the magnetometers measure the three-dimensional magnetic field of the probe. A computer is used for calculating and storing information relative to the position of said probe by using a non-linear computer algorithm.

10 Claims, 3 Drawing Sheets

MEDICAL MAGNETIC POSITIONING SYSTEM AND METHOD FOR DETERMINING THE POSITION OF A MAGNETIC PROBE

TECHNICAL FIELD

The present invention relates to a medical magnetic positioning system (MMAPS) and a method for determining the position of a magnetic probe. More particularly, the present invention relates to a medical magnetic positioning system and a method for determining the position of a magnetic probe inside the body of an individual. While the invention is subject to a wide range of applications, it is especially suited for use for determining the position of a probe in the brain of a person and will be described in that connection.

BACKGROUND ART

Modern intricate surgical procedures often require precise position information about the location of a probe or surgical instrument placed inside a body of an individual. It is desirable to provide this position information without need for large incisions to expose the probe to direct observation. Present x-ray techniques either are not accurate enough or do not have sufficient sensitivity to image very small probes or surgical tools. This is especially a problem in brain surgery where the surgical tool is very small and the ability to determine its precise location is critical to success.

Proposed solutions to this problem have included a controlled mechanical arm with a surgical tool or probe at its distal end. The orientation and translation of the mechanical arm is monitored in order to determine the positions of the probe.

Mechanical arm solutions, however, have several disadvantages. For example, mechanical arm devices are expensive because of the precision required for their construction and for operation. Even with such precision, the accuracy of mechanical arm systems has been limited. Also, mechanical arm systems are restricted to movement of the probes along a linear path. The application of mechanical arm systems is further limited because the body of an individual cannot be moved either during insertion of the probe or thereafter, and the system itself tends to obstruct a surgeon's movements.

In view of the foregoing, a need exists for a relatively inexpensive and accurate means for accomplishing the desired precise measurements without the limitations of the related arts.

DISCLOSURE OF THE INVENTION

Accordingly, the present invention is directed to a medical magnetic positioning system and a method for determining the position of a magnetic probe that substantially overcomes one or more of the problems due to limitations and disadvantages of the related art. The medical magnetic positioning system and the method for determining the position of a magnetic probe contain simpler and less expensive components than those of the related arts and also can yield more accurate results.

Additional features and advantages of the invention will be set forth in the description which follows, and in part will be apparent from the description, or may be learned by practice of the invention. The objectives and other advantages of the invention will be realized and attained by the apparatus and method particularly pointed out in the written description and claims hereof as well as the drawings.

To achieve these and other advantages and in accordance with the purpose of the invention, as embodied and broadly described, the invention provides a method for determining the position of a magnetic probe inside a body of an individual including the steps of fastening at least two spaced magnetometers to an area on an external portion of an individual's body proximate to the desired location of the probe inside of the body, inserting the magnetic probe inside the body of the individual to be spaced from the at least two magnetometers, detecting at the at least two magnetometers the three-dimensional magnetic field of the probe, and determining the location of the probe in accordance with the location of the detected three-dimensional field.

In another aspect the invention provides a medical magnetic positioning system comprising a magnetic probe adapted to be inserted into a body of an individual, at least two triaxial magnetometers adapted to be mounted on an external portion of the body proximate to the inserted location of the probe so that the magnetometers measure the three-dimensional magnetic field of the probe, and a computer for calculating and storing information relative to the position of said probe by using a non-linear computer algorithm.

It is to be understood that both the foregoing general description and the following detailed description are exemplary and explanatory and are intended to provide further explanation of the invention as claimed.

The accompanying drawings are included to provide a further understanding of the invention and are incorporated in and constitute a part of this specification. The drawings illustrate several embodiments of the invention and together with the description serve to explain the principles of the invention.

BRIEF DESCRIPTION OF THE DRAWINGS

In order that the present invention may be more fully understood, it will now be described, by way of example, with reference to the accompanying drawings.

BEST MODE FOR CARRYING OUT THE INVENTION

Figure 1:
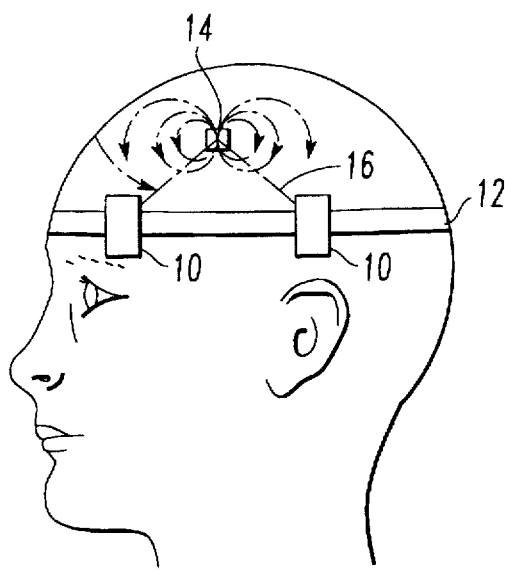
FIG. 1 illustrates typical positions of two magnetometers and the resulting magnetic fields when using the present invention for performing brain surgery.

Reference will now be made in detail to the present preferred embodiments of the invention, examples of which are illustrated in the accompanying drawings. Wherever possible the same reference characters will be used throughout the drawings to designated the same or like parts.

In accordance with the present invention, a method and apparatus are provided by which the position of a magnetic probe inside a body of an individual is displayed and/or recorded by fastening at least two spaced magnetometers to an area on an external portion of an individual's body proximate to the desired location of the probe inside of the body, inserting the magnetic probe inside the body of the individual to be spaced from the at least two magnetometers, and detecting at the magnetometers the three-dimensional magnetic field of the probe. The detected three-dimensional field is then processed by a computer to display the probe location on a monitor screen, as well as to record the probe location on a storage device. The probe may be mounted on a scalpel, catheter or other surgical device capable of being inserted into the body of an individual.

Figure 2:
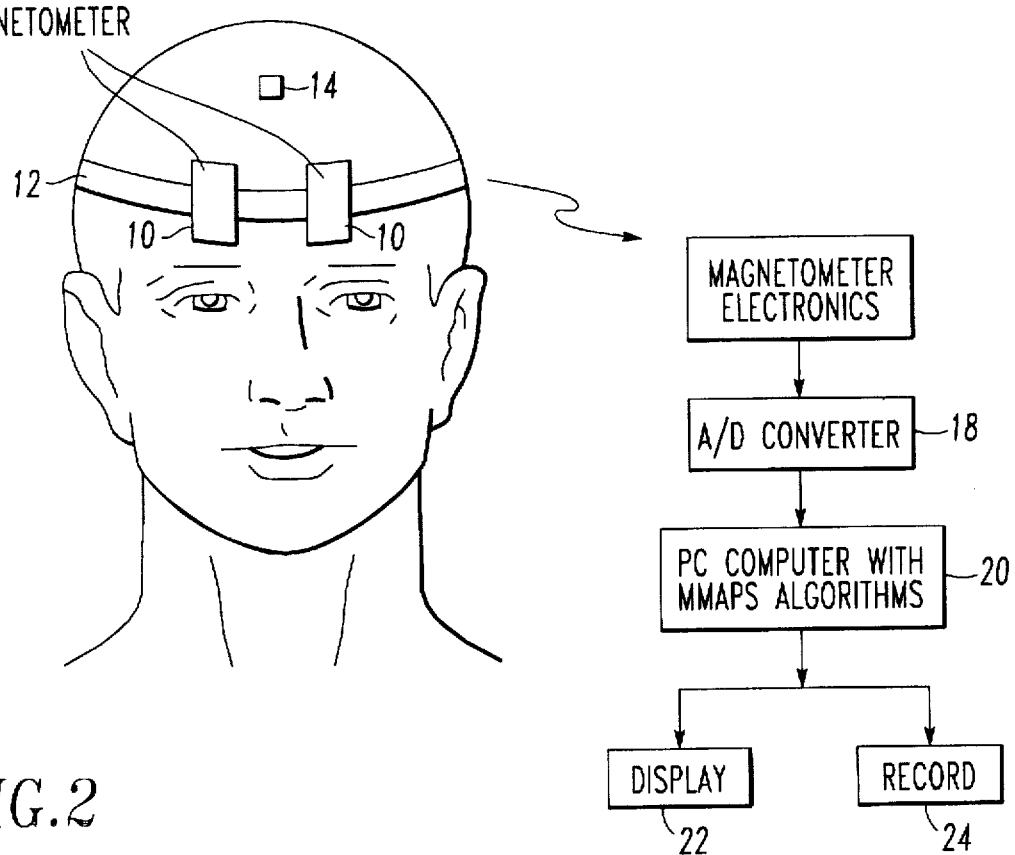
FIG. 2 is a schematic block diagram of one embodiment of the present invention connected to magnetometers fastened to the head of a person.

In an embodiment of the invention illustrated in FIGS. 1 and 2 of the drawings, at least two, preferably two to five magnetometers 10, to be described in more detail below, are supported by a band 12 to be spaced in fixed positions about the head of a person on whom brain surgery is to be performed. A magnetic probe 14, placed on a scalpel or other instrument (not shown) to be used in the surgical procedure, is inserted into the person's brain and located from each of the respective magetometers 10 by a vector 16 having x, y, and z components in a three-dimensional frame of reference.

The magnetic probe 14 can be of any suitable well known type. For example, the magnetic probe can be a small permanent magnet or an AC electromagnet. The small permanent magnet can be a cylinder that is approximately 1 mm in diameter and 2 mm long. Alternatively, the probe can be AC electromagnet that can be a cylinder approximately 1 mm in diameter and 4 mm long.

The AC electromagnet probe has several advantages by comparison to the permanent magnet. While the AC electromagnet may be somewhat larger than the permanent magnet, the AC electromagnet probe can be operated at a preselected frequency well away from any sources of magnetic noise external to the measurement system. That is, the use of an AC electromagnet is advantageous because it can work in a magnetically noisy environment. This is a significant signal-to-noise advantage over the permanent magnet probe. Also, more than one AC probe inside the body can be located by the same magnetometers without any interference between the two probe signals simply by operating the different probes at different frequencies.

Generally, magnetometers are used to sense magnetic fields. Most magnetometers sense magnetic fields in relation to the earth's magnetic field. The use of magnetometers to measure magnetic fields is well described in the literature. For example, J. E. Lenz provides a description of various types of magnetometers in *A Review of Magnetic Sensors*, Proceedings of the IEEE, 78:973–989 (1990).

In the present invention, the magnetometers 10 can be of any suitable known type. In the preferred embodiment of the invention, at least two magnetometers 10 are required and are preferably triaxial fluxgate magnetometers. Generally, the basic fluxgate magnetometer contains a ferromagnetic core wound with a drive coil and a pick-up coil. The component of the magnetic field to be measured along the core axis produces a magnetic flux. Changes of core permeability due to a sinusoidal current in the drive coil cause the core field to change, thereby inducing a voltage in the pick-up coil, at twice the drive frequency, which is proportional to the magnetic field to be measured. Fluxgate magnetometers are described in the literature. For example, F. Primdahl, *The fluxgate magnetometer*, J. Phys. E. Sci. Instrum., 12:241–53 (1979) and M. H. Acura, *Fluxgate Magnetomers for Outer Planets Exploration*, MAG-10:519–523 (1974), provide overviews on fluxgate magnetometers and how magnetic fields are measured.

The sensitivity of the magnetometers should preferably be in the range of 0.1 to 1 nT for useful measurements. This sensitivity range is within the normal operation range of modern fluxgate magnetometers.

In the present invention, by using at least two magnetometers that simultaneously measure the probe's three-dimensional magnetic field, the magnetometer data can be processed in pairs. Using more than one pair of magnetometers allows averaging the results from all possible pairs to improve performance when input signal-to-noise ratios are small.

In an alternate embodiment of the invention, each magnetometer 10 is replaced by a magnetic gradiometer. A magnetic gradiometer consists of two magnetometers spaced closely together. The output signal from the gradiometer is proportional to the difference between the magnetic field values measured at each magnetometer divided by the distance between the magnetometers. The gradiometer embodiment would discriminate against far off magnetic noise sources, such as man made magnetic noise from operating room equipment.

For optimum results, it has been determined that certain surgical instruments which may be magnetic, such as scissors, should be kept at least 2 cm or more away from either the MMAPS transmitter or receiver, that is probe and magnetometer.

In the illustrated embodiment, the probe 14, once inside the brain of the subject individual, provides a magnetic signal that can be measured by the two or more magnetometers 10. More specifically, the magnetometers 10 measure the three-dimensional magnetic field (FIGS. 1 and 2) of the probe 14, which can then be used to provide three-dimensional magnetic induction values $B_{1x}$, $B_{1y}$, $B_{1z}$, at one of the two magnetometers 10, and $B_{2x}$, $B_{2y}$, and $B_{2z}$ at the other.

The magnetic induction values measured by the magnetometers 10 or gradiometer are converted by an analog-to-digital (A/D) converter 18 into digital data suitable for computer processing. The use of an A/D converter is described in literature. The data from the A/D converter concerning the magnetic field of the probe 14, as well as information regarding the position and orientation of the magnetometers is input to a computer 20 having a monitor 22 for a visual display and a storage disc 24 for recording the information. The computer is preferably similar to a 33 Mhz 486 IBM type PC.

Figure 3:
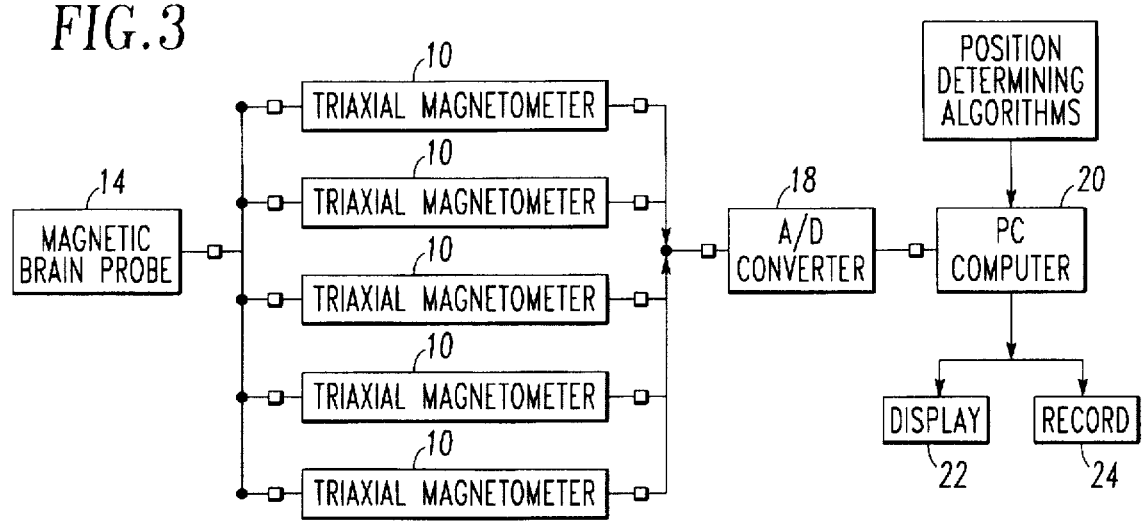
FIG. 3 is a schematic block diagram illustrating a system according to a second embodiment of the present invention.

For purposes of illustration, several magnetometers can be used to measure the probe's magnetic field. For example, in FIG. 3, five magnetometers 10 are represented schematically. As a result, the outputs of the ten different pairs of magnetometers formed from the five magnetometers can be averaged to improve the accuracy of the determined position. Other numbers of magnetometers are possible, but a minimum of two should be used.

The information concerning the probe's magnetic field, and the magnetometers' position and orientation, is used in conjunction with non-linear algorithms to calculate the position of the probe. That is, the computer algorithms invert the magnetic field measurements to yield the probe's three-dimensional position and orientation relative to the magnetometers (FIGS. 1 and 2).

The position determining algorithms use the measurements from at least two magnetometers to determine the orientation and three-dimensional location of the probe. This is accomplished in the following manner. Since the probe is small (preferably 1 mm×4 mm) compared with its distance to the magnetometers (approximately 10 cm for magnetometers placed outside of the skull for a brain probe), the probe is considered a point dipole source of magnetic field. The magnetic probe can act as a transmitter from inside the body of an individual.

Once the probe's position and orientation is calculated using computer algorithms, the computed probe position can be displayed on the monitor of the computer and recorded, for example, on the hard disk of the computer, a floppy disk inserted in the computer, or on external tape drive. At anticipated probe speeds of 2 mm/s, a sampling rate of approximately 4 samples/s provides probe positions approximately every 0.5 mm.

In the present invention, the computer algorithms can be of any suitable well known type. For purposes of illustration, MMAPS algorithms that can be used are provided in a flowchart in FIG. 6 and explained below.

According to the present invention, the computer can perform several mathematical calculations. The x, y, z components of the magnetic induction from a point dipole source at each magnetometer are given by:

$$B_{1x} = \frac{\mu_0}{4\pi r_1^3} \left[ 3x_1 \frac{(\overline{r_1} \cdot \overline{m})}{r_1^2} - m_x \right] \quad (1)$$

$$B_{1y} = \frac{\mu_0}{4\pi r_1^3} \left[ 3y_1 \frac{(\overline{r_1} \cdot \overline{m})}{r_1^2} - m_y \right] \quad (2)$$

$$B_{1z} = \frac{\mu_0}{4\pi r_1^3} \left[ 3z_1 \frac{(\overline{r_1} \cdot \overline{m})}{r_1^2} - m_z \right] \quad (3)$$

$$B_{2x} = \frac{\mu_0}{4\pi r_2^3} \left[ 3x_2 \frac{(\overline{r_2} \cdot \overline{m})}{r_2^2} - m_x \right] \quad (4)$$

$$B_{2y} = \frac{\mu_0}{4\pi r_2^3} \left[ 3y_2 \frac{(\overline{r_2} \cdot \overline{m})}{r_2^2} - m_y \right] \quad (5)$$

$$B_{2z} = \frac{\mu_0}{4\pi r_2^3} \left[ 3z_2 \frac{(\overline{r_2} \cdot \overline{m})}{r_2^2} - m_z \right] \quad (6)$$

where: $\mu_0$=permeability of free space=$4\pi \times 10^{-7}$ weber/meter-ampere $x_1, y_1, z_1$=x,y,z coordinates of the probe with respect to magnetometer 1 (which measures $B_{1x}, B_{1y}, B_{1z}$)

$x_2, y_2, z_2$=x,y,z coordinates of the probe with respect to magnetometer 2 (which measures $B_{2x}, B_{2y}, B_{2z}$)

$m_x, m_y, m_z$=x,y,z components of the probe's magnetic moment m and:

$$r_1 = [x_1^2 + y_1^2 + z_1^2]^{1/2} \quad (7)$$

$$r_2 = [x_2^2 + y_2^2 + z_2^2]^{1/2} \quad (8)$$

The several unknowns in Equations 1–6 can be calculated using several techniques.

In one technique, after the magnetic induction values are calculated from the information provided by the magnetometers, the magnitude of the magnetic moment is inputted to the algorithms. The magnetic moment characterizes the strength of the magnetic probe, its magnitude is generally known, and depends on the type of magnet used in the probe. Thus, although the magnitude of the magnetic moment of the probe may be known, the orientation must be computed.

The components of the magnetic moment m are given in terms of the spherical coordinates θ and φ by:

$$m_x = m \sin\theta \cos\phi \quad (9)$$

$$m_y = m \sin\theta \sin\phi \quad (10)$$

$$m_z = m \cos\phi \quad (11)$$

Figure 4:
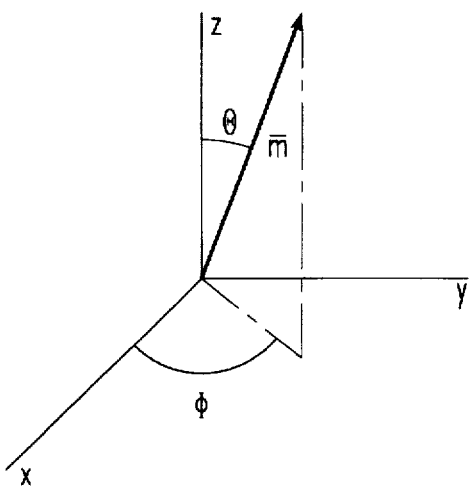
FIG. 4 is a diagram that illustrates the spherical coordinate angles θ and φ, as used in the invention.

These spherical coordinate angles and their mathematical relationships are illustrated in FIG. 4, wherein the magnetic moment is shown as a vector quantity that has an orientation and length.

In the present invention, the displacements of the second magnetometer from the first magnetometer also are accounted for in the computer algorithms. This is done preferably in the following manner: Δx, Δy, Δz each indicate, respectively, the known displacements of the second magnetometer from the first magnetometer, or $x_2, y_2, z_2$ from $x_1, y_1, z_1$. This yields the following mathematical relationships:

$$x_2 = x_1 + \Delta x \quad (12)$$

$$y_2 = y_1 + \Delta y \quad (13)$$

$$z_2 = z_1 + \Delta z \quad (14)$$

Before the unknowns in all of the above equations can be determined, initial trial values for θ, φ $x_1$, $y_1$, and $z_1$ are inputted into the computer. These trial values are required by the numerical solution algorithms. Examples of standard trial values for θ, φ are provided in FIG. 6. Further, the examples of values for $x_1$, $y_1$, and $z_1$ provided in FIG. 6 correspond to roughly half the average diameter of the human skull. Other examples of x, y, and z can be calculated for other parts of the human body by calculating roughly half the average diameter of that part of the body.

Any mathematical constraints are also inputted into the computer before the unknowns are determined. These constraints would specify to the computer that certain variables must be greater or less than some numerical value. The use of mathematical constraints is well known. Examples of mathematical constraints on the spherical coordinate angles for θ, φ are provided in FIG. 6.

Equations 7–14 indicate that the equations for the magnetic induction components (Equations 1–6) can be written in terms of the six variables: m, θ, φ, $x_1$, $y_1$, and $z_1$. Therefore, in principle, equations 1–6 can be solved for these six variables. Since equations 1–6 are non-linear in five of these variables (θ, φ, $x_1$, $y_1$, and $z_1$) numerical iteration is used to obtain a solution. To date, the most successful solution technique has been to measure the magnetic moment m, so it is a known quantity before attempting to solve for the other five variables. This means that there are six equations and only five unknowns, so that there is an over-determined set of equations.

Figure 6:
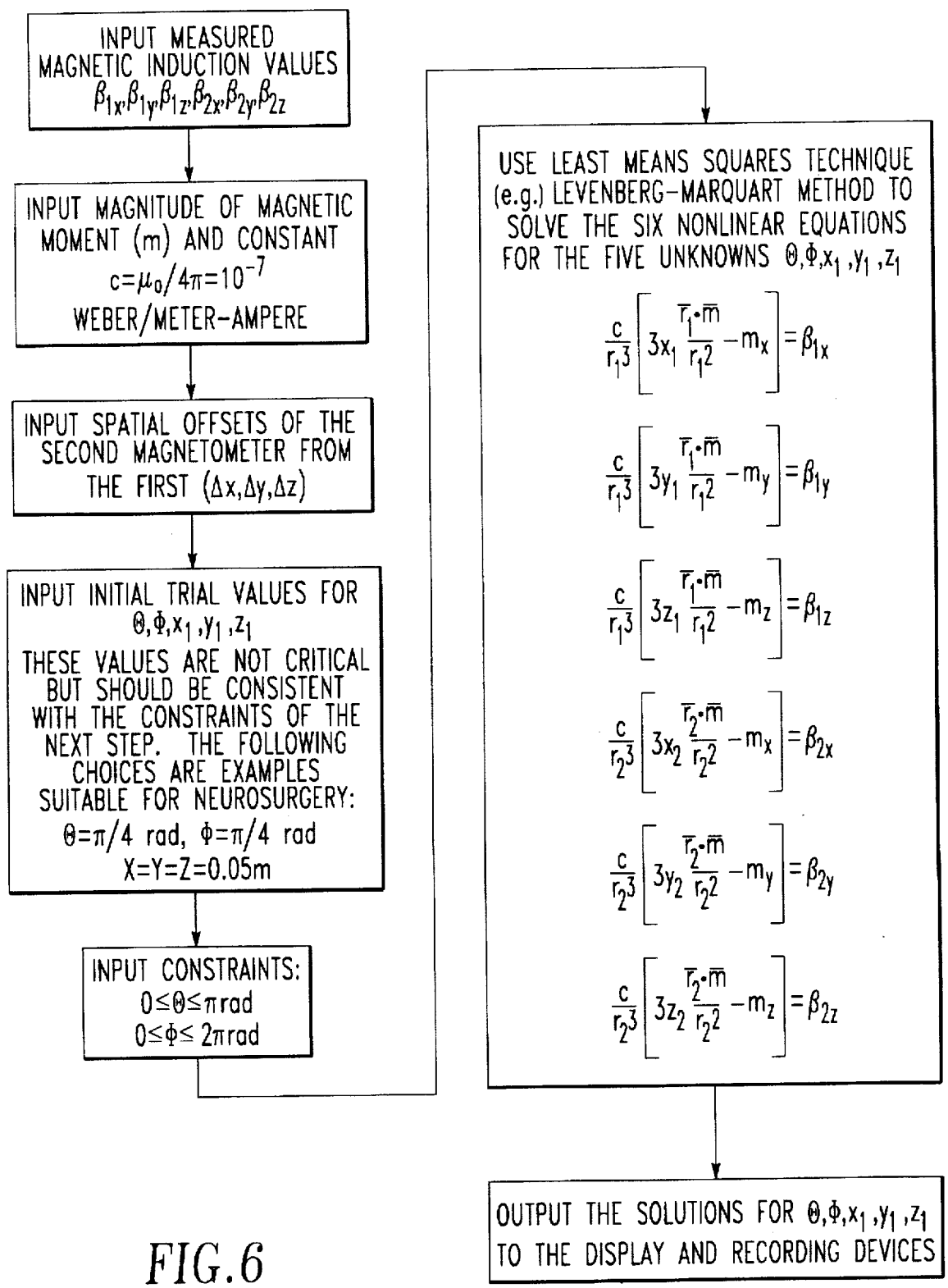
FIG. 6 is a flowchart illustrating the steps in determining the position of a probe in accordance with the present invention.

A standard least-means-square technique (e.g. the Levenberg-Marquart method) for solving over-determined systems of non-linear equations has produced excellent results for solving Equations 1–6 for θ, φ, $x_1$, $y_1$, and $z_1$ (see FIG. 6). Once the unknown values are determined using the least-means-square technique, the orientation and position of the probe are known and displayed on the computer's monitor or other suitable display system. The computer can also store this information on a floppy disk, or any other suitable system for information storage.

Figure 5:
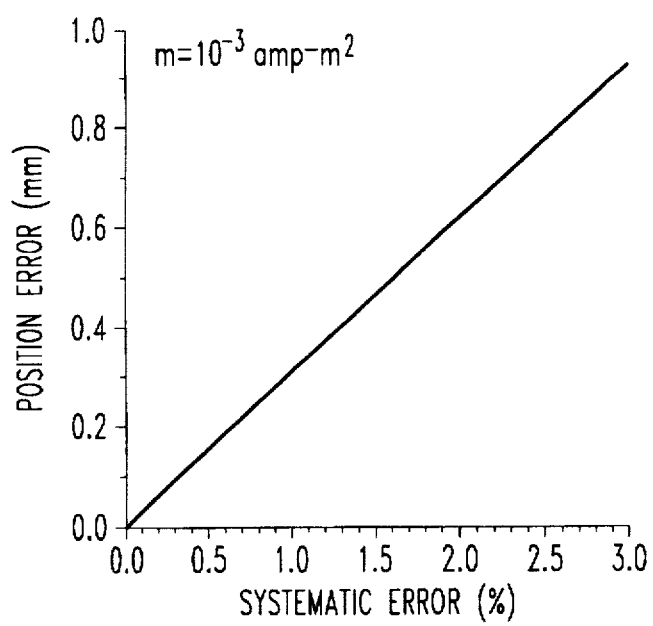
FIG. 5 is a graph that illustrates the position error versus the systematic error, or measurement error, when using the present invention.

The computer can also determine the system's position accuracy as a function of systematic error in the value of the magnetic moment m (or, equivalently, systematic error in measuring the magnetic induction components $B_{1x}, B_{1y}, B_{1z}$, $B_{2x}$, $B_{2y}$, and $B_{2z}$) as is shown in FIG. 5. The average position error (dr) plotted is given by:

$$dr = \sqrt{\frac{dx^2 + dy^2 + dz^2}{3}}$$

where dx, dy, and dz are the errors made in determining $x_1$, $y_1$, and $z_1$. As indicated in FIG. 5, average position errors less than 0.5 mm can be obtained for systematic errors less than 1.5%. The value of the magnetic moment assumed in the figure is $10^{-3}$ amp-m$^2$. This value can be provided by a small cylindrical (1 mm diameter×2 mm long) permanent magnet (made, for example, from neodymium-iron-boron) or a cylindrical AC electromagnet (1 mm diameter×4 mm long) with 100 turns of number 40 AWG wire carrying 0.1 amp.

Although the description of the preferred embodiment has been described in the context of detecting the magnetic signals from a probe in the brain, it is to be understood that the present invention can also detect magnetic signals from other areas of the body, as well as the brain.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

I claim:

1. A method for determining the position of a magnetic probe inside a body of an individual comprising the steps of:

(a) fastening at least two spaced magnetometers to an area on an external portion of the individual's body proximate to the position of the probe inside of the body;

(b) inserting said magnetic probe inside the body of the individual, to be spaced from the at least two magnetometers, said magnetic probe having an a priori known magnetic moment magnitude;

(c) detecting at the at least two magnetometers, the three-dimensional magnetic field of the probe; and (d) determining the location as well as the angular orientation of the probe with respect to the position of the magnetometers by solving simultaneous equations involving the detected three-dimensional field and said magnetic moment magnitude.

2. The method of claim 1, wherein the step of inserting the probe comprises inserting a cylindrical probe approximately 2 mm in length and 1 mm in diameter.

3. The method of claim 1, wherein said probe is an AC magnetic probe.

4. A method for determining the position of a magnetic probe inside a body of an individual comprising the steps of:

(a) placing said magnetic probe inside the body of the individual, said magnetic probe having an a priori known magnetic moment magnitude;

(b) measuring the probe's three-dimensional magnetic field by using a magnetic gradiometer external to the body of the individual; and (c) determining the position, as well as the angular orientation of the probe by a non-linear computer algorithm using the results of said measuring and said magnetic moment magnitude.

5. The method of claim 4, wherein the size of said probe is small, and is approximately 1 mm by 2 mm.

6. The method of claim 4, wherein said probe is an AC magnetic probe.

7. The method of claim 1 or claim 4 wherein said steps of measuring the probe's three-dimensional magnetic field and determining the location of the probe by using a non-linear computer algorithm further comprises:

a. entering into a computer measured magnetic induction values $B_{1x}$, $B_{1y}$, $B_{1z}$, $B_{2x}$, $B_{2y}$, and $B_{2z}$ in which $x_1$, $y_1$, $z_1$=x, y, z coordinates of the probe with respect to a first magnetometer ($B_{1x}$, $B_{1y}$, $B_{1z}$) and $x_2$, $y_2$, $z_2$=x, y, z coordinates of the probe with respect to a second magnetometer ($B_{2x}$, $B_{2y}$, and $B_{2z}$)

b. entering into the computer magnetic moment magnitude, m, of the probe c. entering into the computer a value for a constant, c, wherein $c = \mu_0/4\pi$ in which $\mu_0$=the permeability of free space=$4 \times 10^{-7}$ weber/meter-ampere d. entering into the computer input spatial offsets ($\Delta x$, $\Delta y$, $\Delta z$) of the second magnetometer from the first e. calculating in the computer the following six non-linear equations to determine the values of $\theta$, $\phi$, $x_1$, $y_1$ and $z_1$:

$$\frac{C}{r_1^3}\left[ 3x_1 \frac{(\vec{r_1} \cdot \vec{m})}{r_1^2} - m_x \right] = B_{1x}$$

$$\frac{C}{r_1^3}\left[ 3y_1 \frac{(\vec{r_1} \cdot \vec{m})}{r_1^2} - m_y \right] = B_{1y}$$

$$\frac{C}{r_1^3}\left[ 3z_1 \frac{(\vec{r_1} \cdot \vec{m})}{r_1^2} - m_z \right] = B_{1z}$$

$$\frac{C}{r_2^3}\left[ 3x_2 \frac{(\vec{r_2} \cdot \vec{m})}{r_2^2} - m_x \right] = B_{2x}$$

$$\frac{C}{r_2^3}\left[ 3y_2 \frac{(\vec{r_2} \cdot \vec{m})}{r_2^2} - m_y \right] = B_{2y}$$

$$\frac{C}{r_2^3}\left[ 3z_2 \frac{(\vec{r_2} \cdot \vec{m})}{r_2^2} - m_z \right] = B_{2z}$$

where:

x, y, z are the coordinates of the probe with respect to the first magnetometer $x_2$, $y_2$, $z_2$, the coordinates of the probe with respect to the second magnetometer, are given by:

$x_2 = x_1 + \Delta x$ $x_2 = y_1 + \Delta y$ $z_2 = z_1 + \Delta z$ $x_1$, $y_1$, $z_1$ are the coordinates of the probe with respect to the first magnetometer.

$x_2$, $y_2$, $z_2$ the coordinates of the probe with respect to the second magnetometer, are given by:

$x_2 \geq x_1 + \Delta x$ $y_2 \geq y_1 + \Delta y$ $z_2 \geq z_1 + \Delta z$ $\bar{r}_1$, is a vector with components $x_1$, $y_1$, $z_1$ and magnitude $$\bar{r}_1 = \sqrt{x_1^2 + y_1^2 + z_1^2}$$

$\bar{r}_2$, is a vector with components $x_2$, $y_2$, $z_2$ and magnitude $$\bar{r}_2 = \sqrt{x_2^2 + y_2^2 + z_2^2}$$

m is a vector with components $m_x$, $m_y$, $m_z$ with:

$m_x = m \sin \theta \cos \phi$
$m_y = m \sin \theta \sin \phi$
$m_z = m \cos \theta$ f. outputting the values of $\theta$, $\phi$, $x_1$, $y_1$ and $z_1$ to an output.

8. A medical magnetic positioning system comprising:
   (a) a magnetic probe adapted to be inserted into a body of an individual, said probe having an a priori known magnetic moment magnitude;
   (b) at least two triaxial magnetometers adapted to be mounted on an external portion of the body proximate to an inserted location of the probe so that said magnetometers measure and provide output signals indicative of the three-dimensional magnetic field of the probe; and
   (c) a computer for calculating and storing information relative to the position of said probe, including its angular orientation, by using said output signals and said magnetic moment magnitude in a non-linear algorithm; and
   (d) a display system for displaying the position and angular orientation of said probe.

9. The medical magnetic positioning system of claim 8, wherein the probe is a permanent magnet and the size of said probe is small, and is approximately 1 mm by 2 mm.

10. The medical magnetic positioning system of claim 8, wherein said probe is an AC magnetic probe.

* * * * *